(12) United States Patent
Goodwin et al.

(10) Patent No.: US 8,080,301 B2
(45) Date of Patent: Dec. 20, 2011

(54) ANTI-FOMITIC DEVICES

(76) Inventors: Maureen Goodwin, Staten Island, NY (US); Kathryn A. Trivelli, Staten Island, NY (US); Catherine W. Mooney, Staten Island, NY (US)

( * ) Notice: Subject to any disclaimer, the term of this patent is extended or adjusted under 35 U.S.C. 154(b) by 849 days.

(21) Appl. No.: 11/961,289

(22) Filed: Dec. 20, 2007

(65) Prior Publication Data

US 2009/0162583 A1    Jun. 25, 2009

(51) Int. Cl.
*B32B 9/00* (2006.01)
*B32B 15/04* (2006.01)
*B32B 7/12* (2006.01)
*B65D 65/02* (2006.01)

(52) U.S. Cl. ....... 428/40.1; 438/343; 206/438; 150/154; 150/155; 150/156; 150/157; 150/158; 150/159; 150/160; 150/161; 150/162; 150/163; 150/164; 150/165

(58) Field of Classification Search .................. 428/40.1, 428/40.5, 41.5, 343; 206/438; 150/154–165
See application file for complete search history.

(56) References Cited

U.S. PATENT DOCUMENTS

| | | | | |
|---|---|---|---|---|
| 5,429,377 A * | 7/1995 | Duer | ........................ | 280/33.992 |
| 5,429,631 A * | 7/1995 | Grenier | .................... | 604/385.01 |
| 5,599,093 A * | 2/1997 | Hoftman et al. | ............. | 362/400 |
| 6,021,919 A | 2/2000 | Kelly | | |
| 6,468,611 B1 | 10/2002 | Haskin et al. | | |
| 6,649,236 B2 | 11/2003 | Haskin et al. | | |
| 6,664,309 B2 | 12/2003 | Svenningsen et al. | | |
| 2007/0144929 A1 | 6/2007 | Minerath, III et al. | | |

OTHER PUBLICATIONS

International Search Report and Written Opinion issued for PCT/US08/87444.

* cited by examiner

*Primary Examiner* — Patricia Nordmeyer
(74) *Attorney, Agent, or Firm* — Fox Rothschild LLP; Gerard P. Norton; Jianming J. Hao

(57) ABSTRACT

A sanitary hypo-allergenic latex-free disposable anti-fomitic device is provided. The anti-fomitic device comprises a sheet of a microorganism-impenetrable material comprising a first side and a second side, and a pressure-sensitive adhesive, such as, for example, a covering used in medical tape, covering at least a portion of the first side.

13 Claims, 3 Drawing Sheets

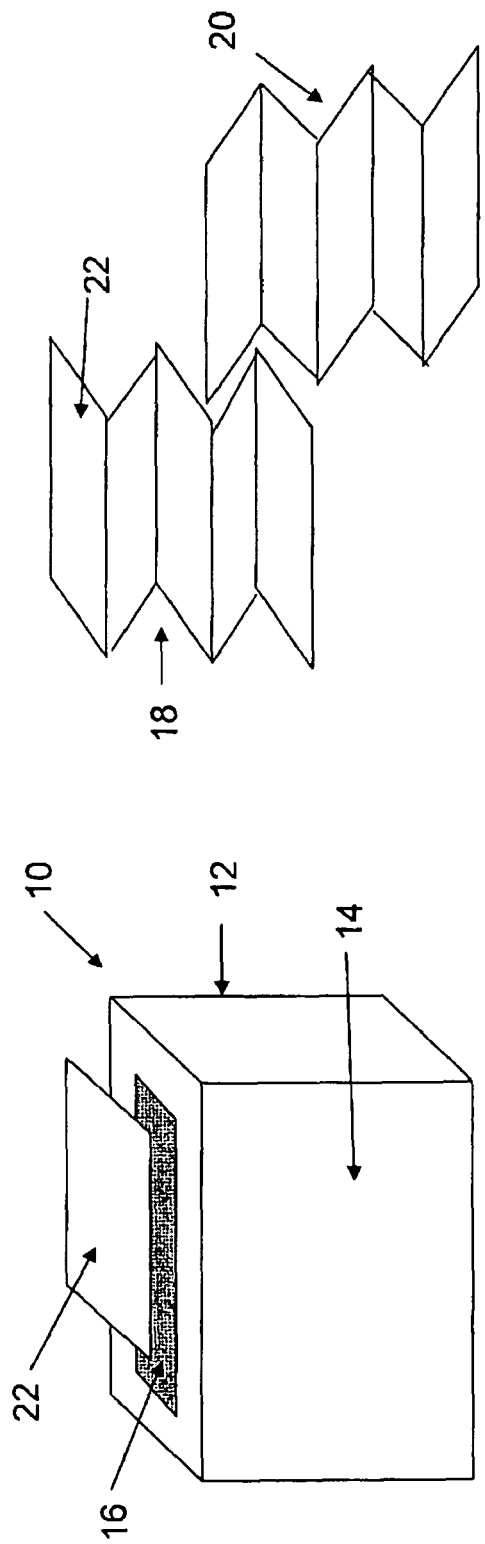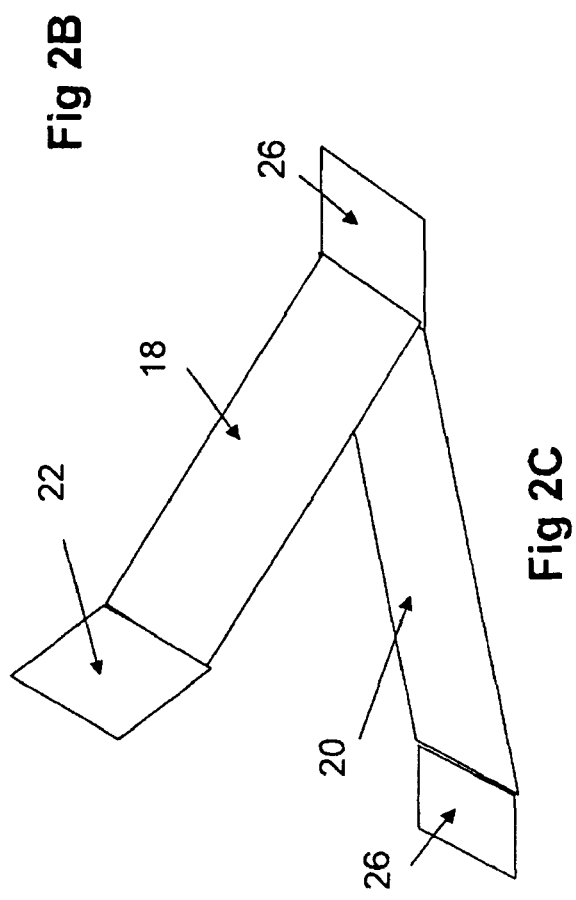
Fig 2A
Fig 2B
Fig 2C

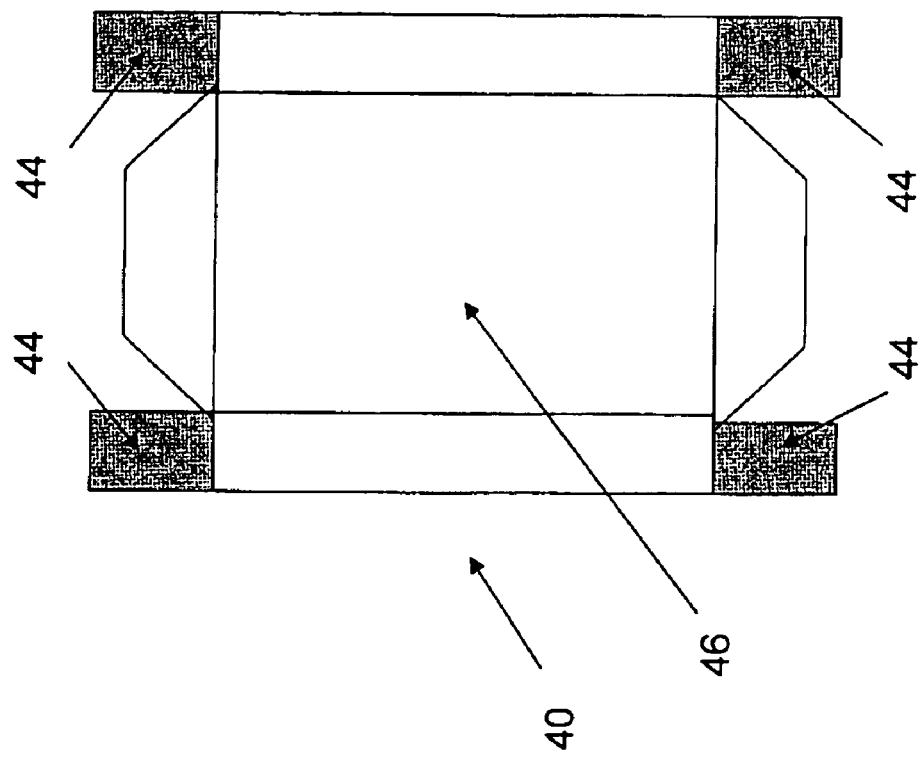
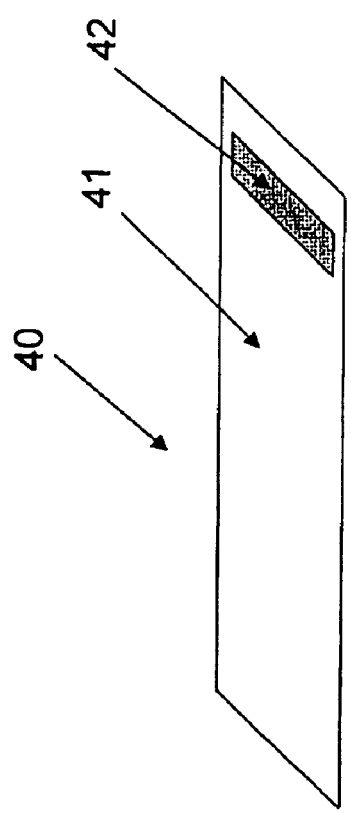
Fig. 3A
Fig. 3B

ANTI-FOMITIC DEVICES

FIELD OF INVENTION

This invention most generally relates to devices for reducing or eliminating the risk of infectious disease transmission through inanimate objects.

BACKGROUND OF INVENTION

Nosocomial infections are those which are a result of treatment in a hospital or a healthcare service unit, but secondary to the patient's original condition. The literature is replete with case reports of fomite transmission in the hospital setting. Health care providers are often cited as the mode of transmission from fomite reservoir to patient.

Gram-positive bacteria are a major cause of nosocomial infection. The most common pathogenic isolates in hospitals include *Enterococcus* spp., *Staphylococcus aureus*, coagulase-negative *staphylococci*, and *Streptococcus pneumoniae* (See, e.g., Principles and Practice of Infectious Diseases, 4th ed. Mandell G L, Bennett J E, Dolin R, ed. Churchill Livingstone, New York 1995), many strains of which are resistant to one or more antibiotics. *Enterococcus* spp. are part of the normal gut flora in humans. Of the more than seventeen enterococcal species, only *E. faecalis* and *E. faecium* commonly colonize and infect humans in detectable numbers (*E. faecalis* is isolated from approximately 80% of human infections, and *E. faecium* from most of the rest).

Nosocomial infections are even more alarming in the 21st century as antibiotic resistance spreads. Vancomycin-resistant *enterococcus* (VRE) spp. are becoming increasingly common in hospital settings. In the first half of 1999, 25.9% of entercoccal isolates from Intensive Care Units were vancomycin-resistant; an increase from 16.6% in 1996 and from 0.4% in 1989. VRE are also commonly resistant to many other commercial antibiotics, including beta-lactams and aminoglycosides. Thus, patients who are immunocompromised or those having a prolonged hospital stay are at increased risk for acquiring a VRE infection.

The problem of antibiotic resistance is not unique to *Enterococcus* spp. Strains of many other potentially pathogenic Gram-positive bacteria displaying antibiotic resistance have been isolated including methicillin-resistant *Staphylococcus aureus* (MRSA), vancomycin-resistant *Staphylococcus aureus* (VRSA), glycopeptide intermediate-susceptible *Staphylococcus aureus* (GISA), vancomycin-resistant MRSA (VR-MRSA) and penicillin-resistant *Streptococcus pneumoniae* (PRSP). Like VRE, therapeutic options for treating infections by these organisms are limited.

The spread and severity of nocosomial infections is due to multiple factors. Hospitals house people who are ill or infected and whose immune systems are often in a weakened state. Increased use of outpatient treatment means that people who are in the hospital are sicker on average. Medical staff move from patient to patient, providing a way for pathogens to spread. Many medical procedures bypass the body's natural protective barriers. Routine use of anti-microbial and antibacterial agents in hospitals creates selection pressure for the emergence of resistant strains.

For centuries it was assumed that infectious diseases were spread primarily by the airborne route or through direct patient contact, and the surrounding environment played little or no role in disease transmission. Up until 1987 the Centers for Disease Control and the American Hospital Association focused on patient diagnosis due to the belief that nosocomial infections were not related to microbial contamination of surfaces. Over the years studies have changed the perspective on infectious disease transmission to include a more complex multifactorial model of disease spread. There is now growing evidence that contaminated surfaces of inanimate objects play a key role in the spread of infectious diseases.

Concern about fomites on medical equipment is heightened when particularly virulent or resistant organisms are identified. Accordingly, there is a need for devices and methods which decrease or eliminate the risk of infectious disease transmission through inanimate objects.

SUMMARY OF INVENTION

The instant invention addresses these and other needs of the prior art by providing, in a first aspect, a hypo-allergenic and latex-free disposable anti-fomitic device comprising: a sheet of a microorganism-impenetrable material comprising a first side and a second side, and a pressure-sensitive adhesive covering at least a portion of the first side.

In a second aspect, the invention provides an article of manufacture comprising: a container having a hollow and an opening; a first and at least a second disposable anti-fomitic device according to the first aspect of invention, located in the hollow of the container, wherein a portion of the first disposable anti-fomitic device extends through the opening, and removal of the first disposable anti-fomitic device extends at least a portion of at least the second anti-fomitic device through the opening.

In a third aspect, the invention provides fomite having a surface, wherein at least a portion of the surface is covered with the anti-fomitic device according to the first aspect of the invention. In different embodiments, the fomite is selected from the group consisting of a blood pressure cuff, EKG leads, a mattress, a stretcher, a tilt table, an ambulatory stretcher chair, an infant weighting scale, a bedside table, a patient chart, poles on gym equipment, an outdoor picnic table, a tray and/or a seat on a baby carriage, and a classroom desk top. The anti-fomitic devices of the instant invention can be placed directly onto a person's skin or onto a fomite creating a protective barrier.

BRIEF DESCRIPTION OF FIGURES

FIGS. 2A-2C illustrate selected embodiment of an article of manufacture incorporating the anti-fomitic device of the instant invention.

FIGS. 3A-B illustrate different embodiments of anti-fomitic devices suitable for using with different fomites.

DETAILED DESCRIPTION OF THE INVENTION

Figure 1:
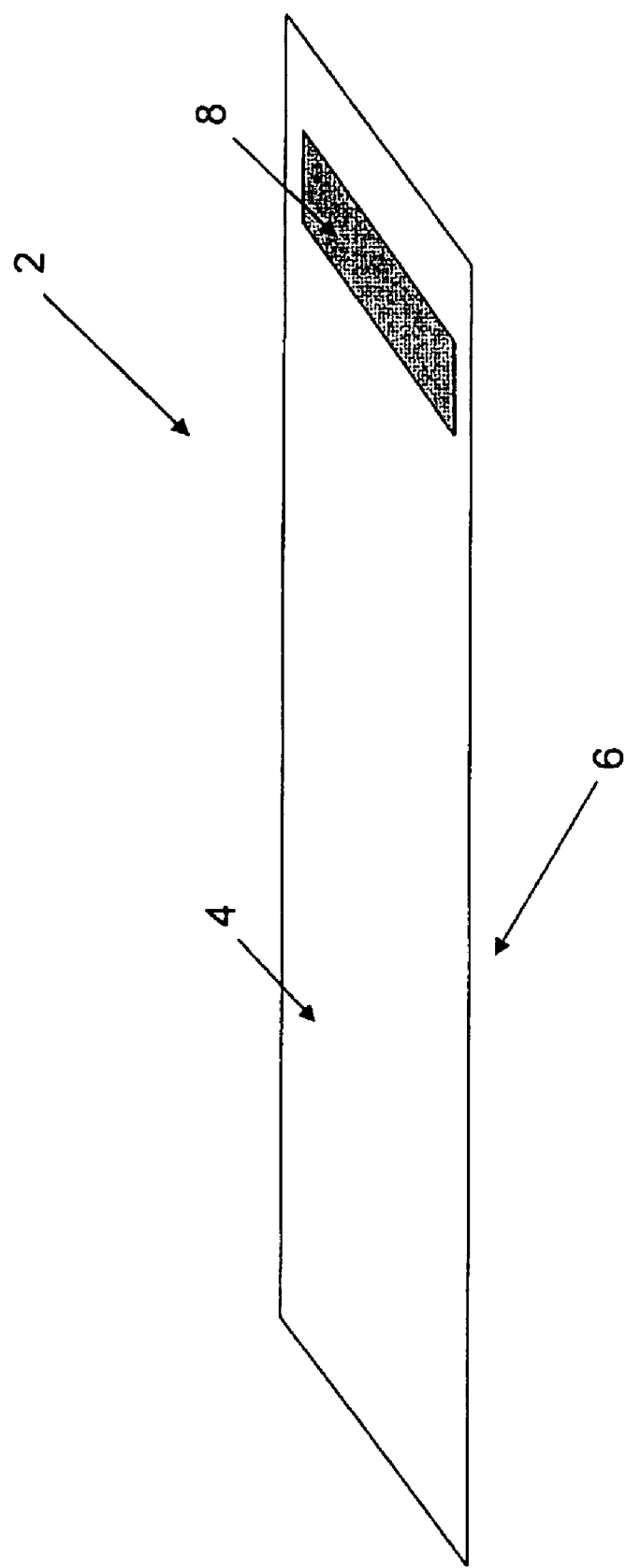
FIG. 1 illustrates an anti-fomitic device according to one embodiment of the instant invention.

Broadly, this invention deals with anti-fomitic devices thus reducing or eliminating a possibility of infections caused by viruses, bacteria, fungi and other microorganisms.

DEFINITIONS

For better understanding of the instant invention, the following non-limiting definitions are provided:

The term "fomite" refers to an inanimate object which harbors microorganisms. In preferred embodiments, fomites are objects which are contacted by multiple persons in public places, and in most preferred embodiments, fomites are the objects which are contacted by multiple infected persons. Suitable non-limiting examples of fomites may be encountered in such places as restaurants, gyms, schools, hospitals, dialysis centers, urgent care centers and ambulance cars.

Fomites consist of both porous and nonporous surfaces or objects that can become contaminated with pathogenic microorganisms and serve as vehicles in transmission. During and after illness, microorganisms are released in large numbers in body secretions, including blood, feces, urine, saliva, and nasal fluid. Fomites become contaminated with the infectious microorganisms by direct contact with body secretions or fluids, contact with soiled hands, contact with aerosolized virus (large droplet spread) generated via talking, sneezing, coughing, or vomiting, or contact with airborne virus that settles after disturbance of a contaminated fomite (i.e., sharing a blood pressure cuff). Once a fomite is contaminated, the transfer of infectious microorganisms may readily occur between inanimate and animate objects, or vice versa, and between two separate fomites (if brought together).

The term "microorganism" is used from a layman's perspective and refers to infection-causing pathogens which cannot be seen with a naked eye. Suitable non-limiting examples of microorganisms include bacteria, viruses, fungi, and protozoans (e.g., amoeba).

The phrase "sheet of a microorganism-impenetrable material" is not to be limited by size or shape.

One object of the invention is to provide a sanitary inexpensive latex-free and hypo-allergenic anti-fomiting device. In one embodiment, shown in FIG. 1, this device comprises a sheet of a microorganism-impenetrable material 2 comprising a first side 4 and a second side 6, and a pressure-sensitive adhesive 8 covering at least a portion of the first side.

Suitable microorganism-impenetrable devices of the instant invention should preferably comport to several criteria, namely, these materials should be inexpensive latex-free and hypoallergenic. Suitable examples of such materials include, without limitation, plastics, such as those selected from the group consisting of polyvinyl chloride, homopolymers polyvinyl chloride, copolymers of polyvinyl chloride, polyesters, polyethylenes, polypropyler and polyolefins, woven or non-woven fabrics, paper-thread or paper-fabric composites. In one embodiment, the anti-fomitic devices of the instant invention are made from paper with a wax treated application. The use of paper treated with wax application provides an additional advantage: the shape of the anti-fomitic device can be adjusted as easily as tearing off the portion which is not needed.

Multiple adhesives are suitable for the instant invention, as long as these adhesives are non-toxic and preferably hypoallergenic and inexpensive. Suitable pressure sensitive adhesives are well known to those of skill in the art.

In different embodiments, the non-limiting examples of such adhesives include an acryl resin, a vinyl acryl resin, acetate/ethylene, polyvinyl acetate, and the like, such as styrene/butadiene rubbers, vinyl acetate/ethylene, vinyl acetate/acrylates, polyvinyl chloride, polyvinyl alcohols, polyurethanes, vinyl acetates, acryl/vinyl acetates, and the like, rubber gum adhesives and other synthetic adhesives, which, preferably, are non-latex-based.

Reports of occurrence of antibiotic-resistant bacterial infections are now on the rise. The incidence of such antibiotic-resistant bacteria (and, possibly, other microorganisms) is due, at least in part, to widespread use of antibiotics. These antibiotic-resistant microorganisms provide serious public health risks. Non-limiting examples of such antibiotic-resistant microorganisms include, without limitations, bacteria selected from the group comprising *Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pediococcus, Bacillus, Corynebacterium, Arcanobacterium, Actinomyces, Rhodococcus, Listeria, Erysipelothrix, Gardnerella, Neisseria, Campylobacter, Arcobacter, Wolinella, Helicobacter, Achromobacter, Acinetobacter, Agrobacterium, Alcaligenes, Chryseomonas, Comamonas, Eikenella, Flavimonas, Flavobacterium, Moraxella, Oligella, Pseudomonas, Shewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thermoactinomycetes, Mycobacterium, Treponema, Borrelia, Leptospira,* and Chlamydiae.

In one embodiment, the infection is caused by metricilin-resistant *S. Aureus* (MRSA), vancomycin-resistant *S. Aureus* or vancomycin-resistant *enterococcus*.

Accordingly, if the use of antibiotics is eliminated or diminished, the incidence of antibiotic resistance would likely decrease. In one embodiment, the instant invention serves this goal by achieving its intended purpose without the use of microorganism-killing compounds. The choice of materials used for the anti-fomitic devices of the instant invention eliminate the necessity of using anti-microbial and anti-bacterial agents with the devices of the instant invention hence reducing the incidents of creating bacterial and/or viruses resistant to antibiotics (Superbugs).

The anti-fomitic devices may be incorporated or used together with multiple articles of manufacture. For example, in one embodiment shown in FIG. 2A, the invention provides an article of manufacture 10 comprising a container 12 having a hollow 14 and an opening 16, a first and at least a second disposable anti-fomitic devices (18 and 20 respectively, see FIG. 2b) located in the hollow of the container, wherein a portion 22 of the first disposable anti-fomitic device extends through the opening, and removal of the first disposable anti-fomitic device extends at least a portion of at least the second anti-fomitic device through the opening. In one embodiment illustrated in FIG. 2B, the first and at least the second anti-fomitic devices are pre-folded in such a way that some folds of at least the second anti-fomitic device are located between the folds of the first anti-fomitic device: thus when the user pulls the first anti-fomitic device out of the container, a portion of at least the second anti-fomitic device is also pulled through the container's opening. In another embodiment, illustrated in FIG. 2C, the first and the second anti-fomitic devices 18 and 20 releasably adhere to each other by the pressure sensitive adhesive 26. The pressure sensitive adhesive provides sufficient adhesive force to pull a portion of at least the second anti-fomitic device when the first anti-fomitic device is removed from the article of manufacture.

Suitable containers include cardboard boxes, paper boxes, plastic boxes, and the like. The articles of manufacture described herein may be used in fomite-rich areas (e.g., hospitals), for example, laying on a table or attached to a wall.

In different embodiments of the invention, the anti-fomitic devices may be used for covering the fomites. Non-limiting examples of such fomites include a blood pressure cuff, EKG leads, a mattress, a stretcher, a tilt table, an ambulatory stretcher chair, an infant weighting scale, a bedside table, and a patient chart, gym equipment, an outdoor picnic table, a tray and/or a seat on a baby carriage, and a classroom desk top, and an outdoor picnic table. The shape of the anti-fomitic device of the instant invention, as well as the portion covered with the adhesive depends on the nature of the fomite. For example, if the fomite is a blood pressure cuff, the suitable anti-fomitic devices may come in several sizes depending on the size of the cuff and/or the size of the arm of the subject: e.g., sizes suitable for infants and children, and sizes suitable for adults. For example, in one embodiment, illustrated in FIG. 3A, the anti-fomitic device 40 comprises a band of a suitable material 41, such as, for example, wax paper with a portion 42 covered with adhesive. In another embodiment, particularly suitable for use with such fomites as mattresses, the anti-fomitic device may be in a shape illustrated in FIG. 3B, with adhesive-covered portions 44 and portion 46 located on top of the mattress.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A sanitary disposable anti-fomitic device comprising: a sheet of a microorganism-impenetrable material comprising a first side and a second side, and a pressure-sensitive adhesive covering at least a portion of the first side, wherein the anti-fomitic device is hypo-allergenic and does not contain latex and does not contain an antibiotic.

2. The disposable anti-fomitic device of claim 1, wherein the microorganism-impenetrable material is paper treated with a wax application.

3. The disposable anti-fomitic device of claim 1, wherein the pressure-sensitive adhesive comprises an acrylate copolymer.

4. The disposable anti-fomitic device of claim 1, wherein the microorganism is selected from the group comprising *Salmonella, Shigella, Escherichia, Enterobacter, Serratia, Proteus, Yersinia, Citrobacter, Edwardsiella, Providencia, Klebsiella, Hafnia, Ewingella, Kluyvera, Morganella, Planococcus, Stomatococcus, Micrococcus, Staphylococcus, Vibrio, Aeromonas, Plessiomonas, Haemophilus, Actinobacillus, Pasteurella, Mycoplasma, Ureaplasma, Rickettsia, Coxiella, Rochalimaea, Ehrlichia, Streptococcus, Enterococcus, Aerococcus, Gemella, Lactococcus, Leuconostoc, Pediococcus, Bacillus, Corynebacterium, Arcanobacterium, Actinomyces, Rhodococcus, Listeria, Erysipelothrix, Gardnerella, Neisseria, Campylobacter, Arcobacter, Wolinella, Helicobacter, Achromobacter, Acinetobacter, Agrobacterium, Alcaligenes, Chryseomonas, Comamonas, Eikenella, Flavimonas, Flavobacterium, Moraxella, Oligella, Pseudomonas, Shewanella, Weeksella, Xanthomonas, Bordetella, Franciesella, Brucella, Legionella, Afipia, Bartonella, Calymmatobacterium, Cardiobacterium, Streptobacillus, Spirillum, Peptostreptococcus, Peptococcus, Sarcinia, Coprococcus, Ruminococcus, Propionibacterium, Mobiluncus, Bifidobacterium, Eubacterium, Lactobacillus, Rothia, Clostridium, Bacteroides, Porphyromonas, Prevotella, Fusobacterium, Bilophila, Leptotrichia, Wolinella, Acidaminococcus, Megasphaera, Veilonella, Norcardia, Actinomadura, Norcardiopsis, Streptomyces, Micropolysporas, Thermoactinomycetes, Mycobacterium, Treponema, Borrelia, Leptospira,* and Chlamydiae.

5. The disposable anti-fomitic device of claim 1, wherein the microorganism is antibiotic-resistant strain of *S. Aureus*.

6. The disposable anti-fomitic device of claim 1, wherein said disposable anti-fomitic device is folded in such a way that said disposable anti-fomitic device has a plurality of folds.

7. The disposable anti-fomitic device of claim 6, wherein at least one fold of said plurality of folds is located between folds of another disposable device that is identical to said disposable anti-fomitic device.

8. The disposable anti-fomitic device of claim 7, whereby, if one of said disposable anti-fomitic device and said disposable device is pulled, the other of said two devices is also pulled.

9. The disposable anti-fomitic device of claim 6, wherein at least a part of said disposable anti-fomitic device is located between folds of another disposable device that is identical to said disposable anti-fomitic device.

10. The disposable anti-fomitic device of claim 9, whereby, if one of said disposable anti-fomitic device and said disposable device is pulled, the other of said two devices is also pulled.

11. The disposable anti-fomitic device of claim 1, wherein said disposable anti-fomitic device releasably adheres, by said pressure-sensitive adhesive, to another disposable device that is identical to said disposable anti-fomitic device.

12. The disposable anti-fomitic device of claim 11, whereby, if one of said disposable anti-fomitic device and said disposable device is pulled, the other of said two devices is also pulled.

13. The disposable anti-fomitic device of claim 1, wherein said disposable anti-fomitic device comprises two or more discrete adhesive-covered portions.

* * * * *